(12) United States Patent
Chang

(10) Patent No.: US 7,435,800 B2
(45) Date of Patent: Oct. 14, 2008

(54) ANTIBODIES TO INTERLEUKIN-20 AND METHOD FOR INHIBITING INTERLEUKIN-20 INDUCED CELL PROLIFERATION

(75) Inventor: Ming-Shi Chang, Tainan (TW)

(73) Assignee: Chi-Mei Medical Center, Tainan (TW)

( * ) Notice: Subject to any disclaimer, the term of this patent is extended or adjusted under 35 U.S.C. 154(b) by 282 days.

(21) Appl. No.: 11/298,329

(22) Filed: Mar. 2, 2006

(65) Prior Publication Data

US 2006/0142550 A1    Jun. 29, 2006

Related U.S. Application Data

(63) Continuation-in-part of application No. 10/444,765, filed on May 23, 2003, now abandoned.

(60) Provisional application No. 60/634,642, filed on Dec. 9, 2004.

(51) Int. Cl.
*C07K 16/00*    (2006.01)

(52) U.S. Cl. .............................. 530/388.23; 530/387.2
(58) Field of Classification Search ...................... None
See application file for complete search history.

(56) References Cited

OTHER PUBLICATIONS

Hunt et al., "Ultraviolet B Light Stimulates Interleukin-20 Expression by Human Epithelial Keratinocytes," *Photochemistry and Photobiology*, Sep./Oct. 2006, vol. 82, pp. 1292-1300.
Hsieh et al., "Interleukin-20 promotes angiogenesis in a direct and indirect manner," *Genes and Immunology*, 2006, vol. 7, pp. 234-242.
International Search Report and Written Opinion for International Application No. PCT/US2006/46802, dated Dec. 19, 2007, 8 pages.

*Primary Examiner*—Prema Mertz
(74) *Attorney, Agent, or Firm*—Occhiuti Rohlicek & Tsao LLP

(57) ABSTRACT

Antibody to human IL-20 protein, a method for generation thereof and cells producing this antibody are disclosed. The antibody of the present invention has specificity to neutralizing hIL-20W-induced CPAE proliferation activity, and is useful for treating IL-20-induced inflammation, such as artheriosclerosis and rheumatoid arthritis.

1 Claim, 8 Drawing Sheets

US 7,435,800 B2

ANTIBODIES TO INTERLEUKIN-20 AND METHOD FOR INHIBITING INTERLEUKIN-20 INDUCED CELL PROLIFERATION

REFERENCE TO RELATED APPLICATIONS

This application is a Continuation-in-Part of U.S. patent application Ser. No. 10/444,765, filed May 23, 2003, now abandoned. This application also claims priority to U.S. Provisional Application Ser. No. 60/634,642, filed Dec. 9, 2004. The disclosure of which is incorporated herein by reference.

BACKGROUND OF THE INVENTION

1. Field of the Invention

The present invention provides a monoclonal antibody having specificity in neutralizing hIL-20W-induced calf pulmonary artery endothelial cells. The antibody may be used to treat IL-20 inflammation, including artheriosclerosis and rheumatoid arthritis.

2. Description of the Related Art

Inflammatory response is a key component of host defense, but excessive inflammation, such as occurs in arthritis or septic shock, can be harmful or even fatal. Interleukin (IL)-10 was originally described as a cytokine synthesis inhibitory factor because of its inhibitory effect on cytokine production. Because IL-10 suppresses the release and function of a number of proinflammatory cytokines such as IL-1, tumor necrosis factor (TNF)-α, and IL-6, it is a normal endogenous feedback factor for the control of immune responses and inflammation. Autoimmune models of rheumatoid arthritis, thyroiditis, and collagen-induced arthritis, as well as a model of herpetic stromal keratitis, suggest the negative regulatory roles of IL-10 on inflammation and immunopathology. However, IL-10 is also a stimulatory factor for mast cells, B cells, and thymocytes; it is pleiotropic and acts on many other cell types, including monocytes macrophages, T cells, natural killer (NK) cells, neutrophils, endothelial cells, and peripheral blood mononuclear cells (PBMCs). IL-10 can inhibit the generation of new vessels within tumors both directly by acting on the tumor cells and indirectly by influencing infiltrating immune cells. Atherosclerosis is a chronic inflammatory disease of the arterial wall characterized by the progressive accumulation of lipids, extracellular matrix, and cells, including macrophages, T lymphocytes, and smooth muscle cells. Inflammation plays a major role in atherosclerosis plaque disruption and thrombosis, and therefore greatly influences the occurrence of coronary syndromes and mortality. IL-10, important in atherosclerosis lesion formation and stability, is a protective factor against the effect of environmental pathogens on atherosclerosis.

Several new members of the IL-10 family, including IL-19, IL-20, IL-22, MDA-7 (IL-24), and AK155 (IL-26), have only recently been discovered. IL-19 was first discovered in LPS-treated monocytes. IL-19 induces the production of IL-6 and TNF-α from monocytes and of Th2 cytokines from CD4+ T cells, and is associated with asthma.

IL-20 is preferentially expressed in monocytes. Overexpression of IL-20 in transgenic mice causes neonatal death as well as skin abnormalities, including aberrant epidermal differentiation. IL-20 selectively enhances multipotential hematopoietic progenitors in vitro and in vivo. IL-20 induces STAT 3 activation through binding to two types of IL-20 receptor (R) complexes, either IL-20RI and IL-20R2 or IL-20R2 and IL-22R. Stimulation of HepG2 human hepatoma cells with IL-22 upregulates the production of acute phase reactants like serum amyloid A, α1-antichymotrypsin, and haptoglobin. IL-22 plays a protective role in T-cell-mediated murine hepatitis and increases the innate immunity of tissues. Expression of IL-24 was upregulated in wound healing and during the in vitro differentiation of a melanoma cell line. IL-26 is induced by the transformation of T lymphocytes with *Herpesvirus Saimiri*, and targets epithelial cells through IL-20R1 and IL-10R2.

Little is known about the in vitro biologic function of IL-20, except that it induces the proliferation of keratinocytes. Our aims, therefore, were to explore whether IL-20 acts on target cells other than keratinocytes. We also wanted to analyze whether IL-20, like IL-10, has any association with inflammatory diseases such as atherosclerosis and rheumatoid arthritis; thus, we treated calf pulmonary artery endothelial cells (CPAEs) with human (h)IL-20 and monitored the proliferation of the cells. We also treated the endothelial cells with both IL-10 and IL-20 and demonstrated that IL-10 antagonized the activity of IL-20. ApoE-deficient (ApoE$^{-/-}$) mice reveal the phenotype of atherosclerosis. Therefore, we performed immunohistochemical staining on the aortic arch of ApoE$^{-/-}$ mice and demonstrated that IL-20 was expressed on atherosclerotic plaque and that its receptors, IL-20RI and IL-20R2, were upregulated on the endothelium and atherosclerotic plaque.

SUMMARY OF THE INVENTION

An object of the present invention is to develop an anti-interleukin-20 monoclonal antibody.

Another object of the present invention is to develop a method of inducing proliferation of calf pulmonary artery endothelial cell (CPAE), which comprises the steps of:

a) preparing a CPAE cell culture at a predetermined density;

b) treating CPAE cell culture with interleukin-20 at a proliferation inducing concentration; and c) incubating said interleukin-20 treated CPAE cell culture.

A further object of the present invention is to develop a method of inhibiting interleukin-20 induced proliferation of calf pulmonary artery endothelial cell (CPAE), which comprises the steps of:

a) preparing a CPAE cell culture at a predetermined density;

b) incubating interleukin-20 with an interleukin-20 binding agent in an amount excessive of the amount of interleukin-20 to neutralize interleukin-20;

c) adding said neutralized interleukin-20 to said CPAE cell culture; and d) incubating said CPAE cell culture with said neutralized interleukin-20.

(A) Screening in human cDNA libraries, hIL-20 wild-type (W) (607 bp) is expressed in kidney (i), lung (ii), and placenta (iii) tissue; hIL-20 short-form (S) (532 bp) is expressed only in lung (ii) tissue. Tissues without IL-20 transcripts are not shown. (B) Comparison of amino acid sequences between hIL-20W (SEQ ID NO: 1) and hIL-20s (SEQ ID NO: 2). Human IL-20W has 5 exons and 4 introns in the coding region. Exon 4 is deleted in hIL-20s. The locations of exon-lintron junctions of the hIL-20 gene are indicated by ▼. Deleted exons in the short-forms are indicated by dashes.

Figure 2:
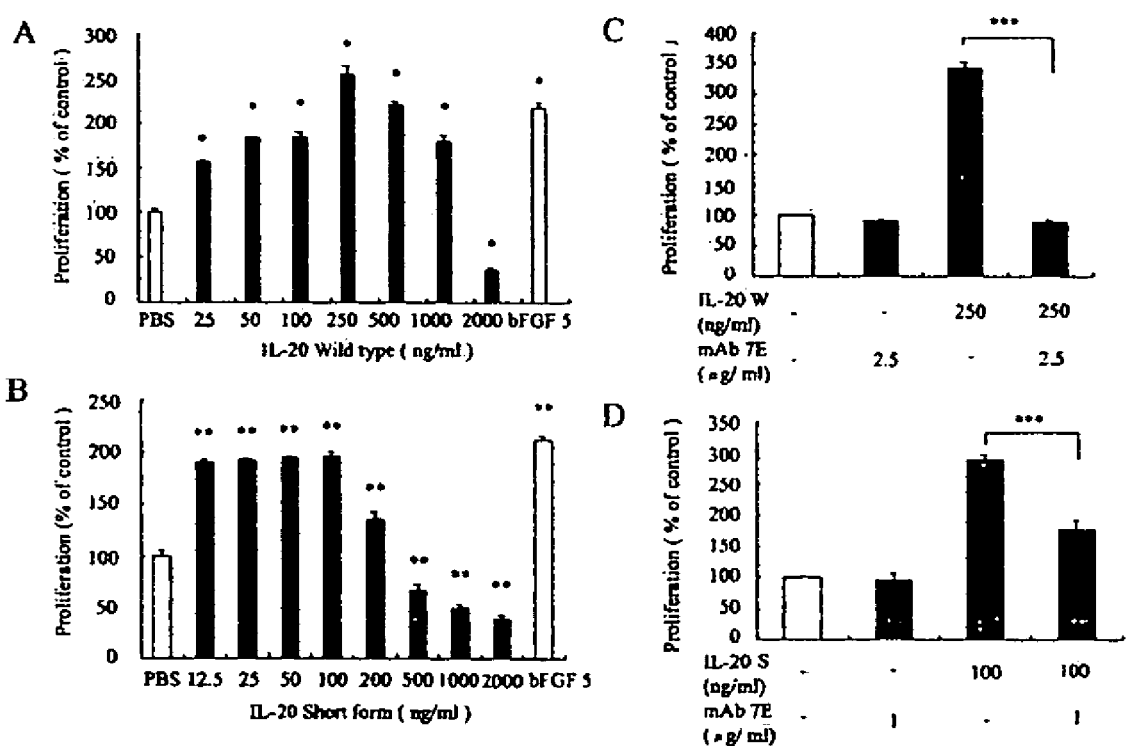

FIG. 2. Effect of human (h)IL-20 on proliferation of calf pulmonary artery endothelial cells (CPAEs).

CPAEs (1×10) were incubated with various concentrations of hIL-20W (wild-type) or short-form (hIL-20S) for 72 hours. At the end of incubation, 1 mg/ml solution of MTT was added to the cells and incubated for another 4 hours. Cell numbers were determined as absorbance at an optical density of 550 nm. The results of hIL-20-treated cells were expressed as a percentage of untreated control cells. bFGF was used as the positive control in the cell proliferation assay. (A) hIL-20W at concentrations between 25 ng/ml and 1000 ng/ml induced CPAE proliferation. (B) hIL-20S at concentrations between 12 ng/ml and 100 ng/ml induced CPAE proliferation. (C) The optimal concentration of hIL-20W (250 ng/ml) was incubated with CPAEs. Monoclonal antibody 7E (2.5 μg/ml) alone was added to the cells as a control or incubated with hIL-20W together before being added to CPAEs. Cell proliferation was monitored using MTT. (D) Neutralization activity of 7E on hIL-20S. The experiment was performed as described in (C) except that 1 μg/ml of 7E and the optimal concentration of hIL-20s (100 ng/ml) were used. Data represent means±SD of triplicate experiments. The experiment was repeated five times with similar results. *$P<0.05$ compared with PBS in (A). $P<0.05$ compared with PBS in (B). *$P<0.05$ compared with hIL-20-stimulated CPAEs in (C) and (D).

Figure 3:
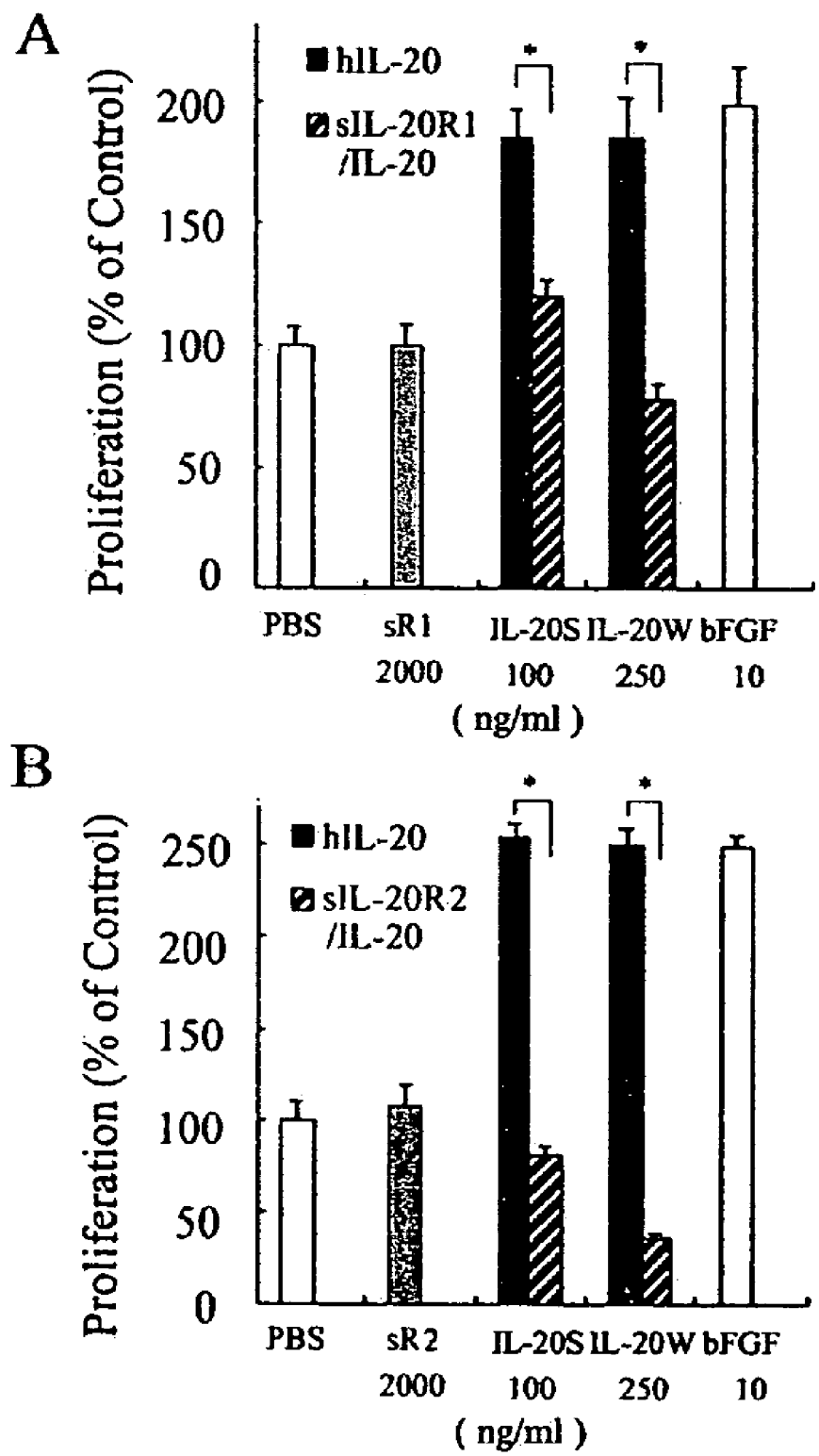

FIG. 3. Human soluble (s)IL-20R1 or sIL-20R2 protein neutralized human (h)IL-20-induced proliferation of calf pulmonary artery endothelial cells (CPAEs).

Human IL-20W (wild-type) (250 ng/ml) or hIL-20s (short-form) (100 ng/ml) was incubated with sIL-20R1 or sIL-20R2 (2 μg/ml) before being added to the cells. The gray bar indicates treatment with sIL-20R1I or sIL-20R2 alone. The black bars indicate treatment with hIL-20W or hIL-20s alone. The hatched bars stand for treatment with both hIL20 and soluble receptors together. (A) Neutralization by sIL-20R1. (B) Neutralization by sIL-20R2. Data represent means±SD of triplicate experiments. *$P<0.05$ compared with hIL-20-stimulated CPAEs.

Figure 4:
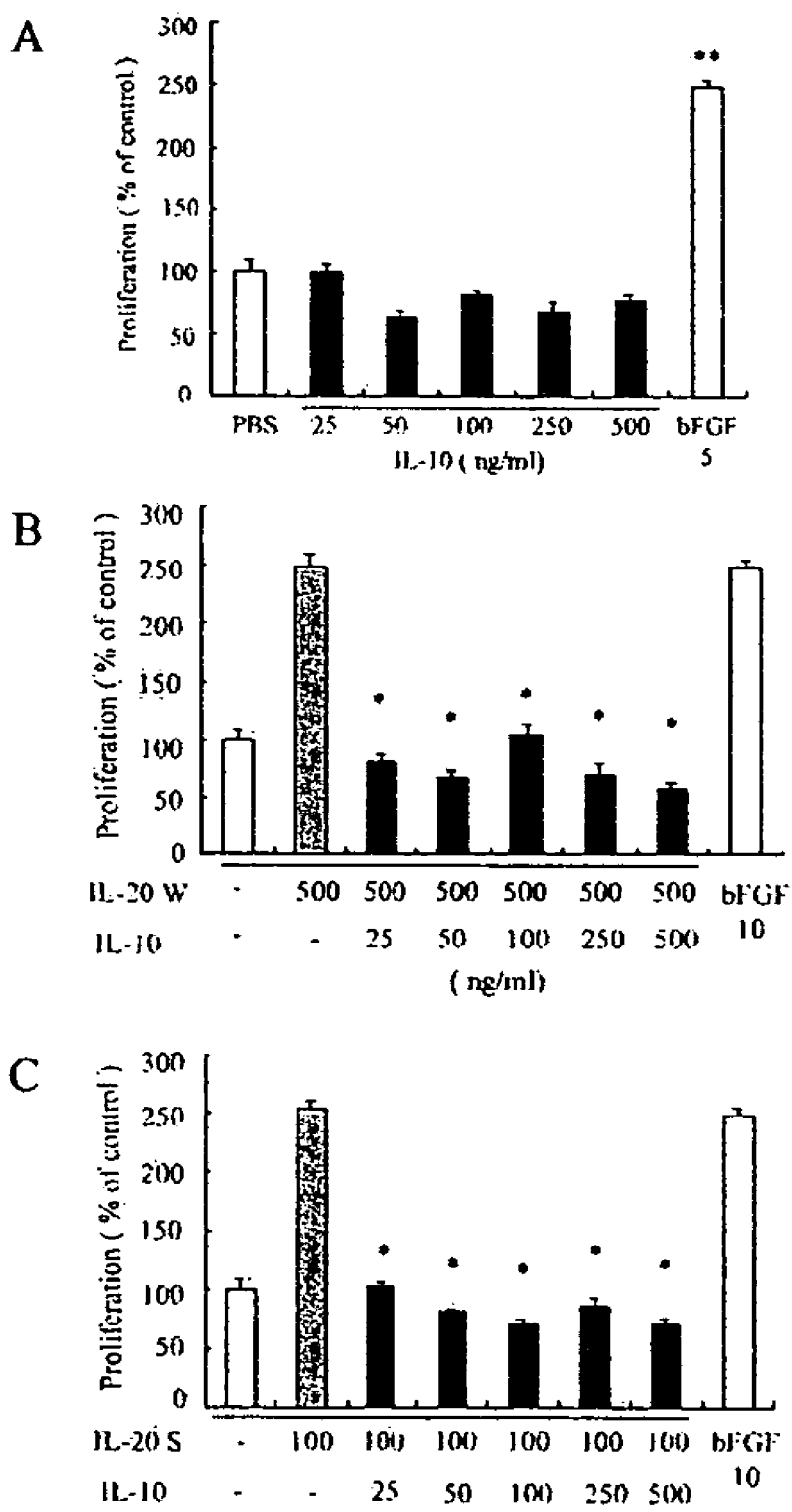

FIG. 4. Interaction of IL-10 and human (h)IL-20 on proliferation of calf pulmonary artery endothelial cells (CPAEs).

(A) Various concentrations of IL-10 (25 ngtml-500 ng/ml) were added to CPAEs and proliferation was monitored. (B) The optimal concentration of hIL-20 wild-type (500 ng/ml) was mixed with various concentrations of IL-10 (25 ng/ml-500 ng/ml) and incubated with CPAEs. The effect of IL-10 on hIL-20 wild-type-induced proliferation of CPAEs was monitored using an MTT assay. (C) The experiment was performed as in (B) except that the optimal concentration of hIL-20 short-form (100 ng/ml) was incubated with various concentrations of IL-10 (25 ng/ml-500 ng/ml). Data represent means±SD of triplicate experiments. *$P<0.05$ compared with hIL-20-stimulated CPAEs. **$P<0.05$ compared with PBS.

Figure 5:
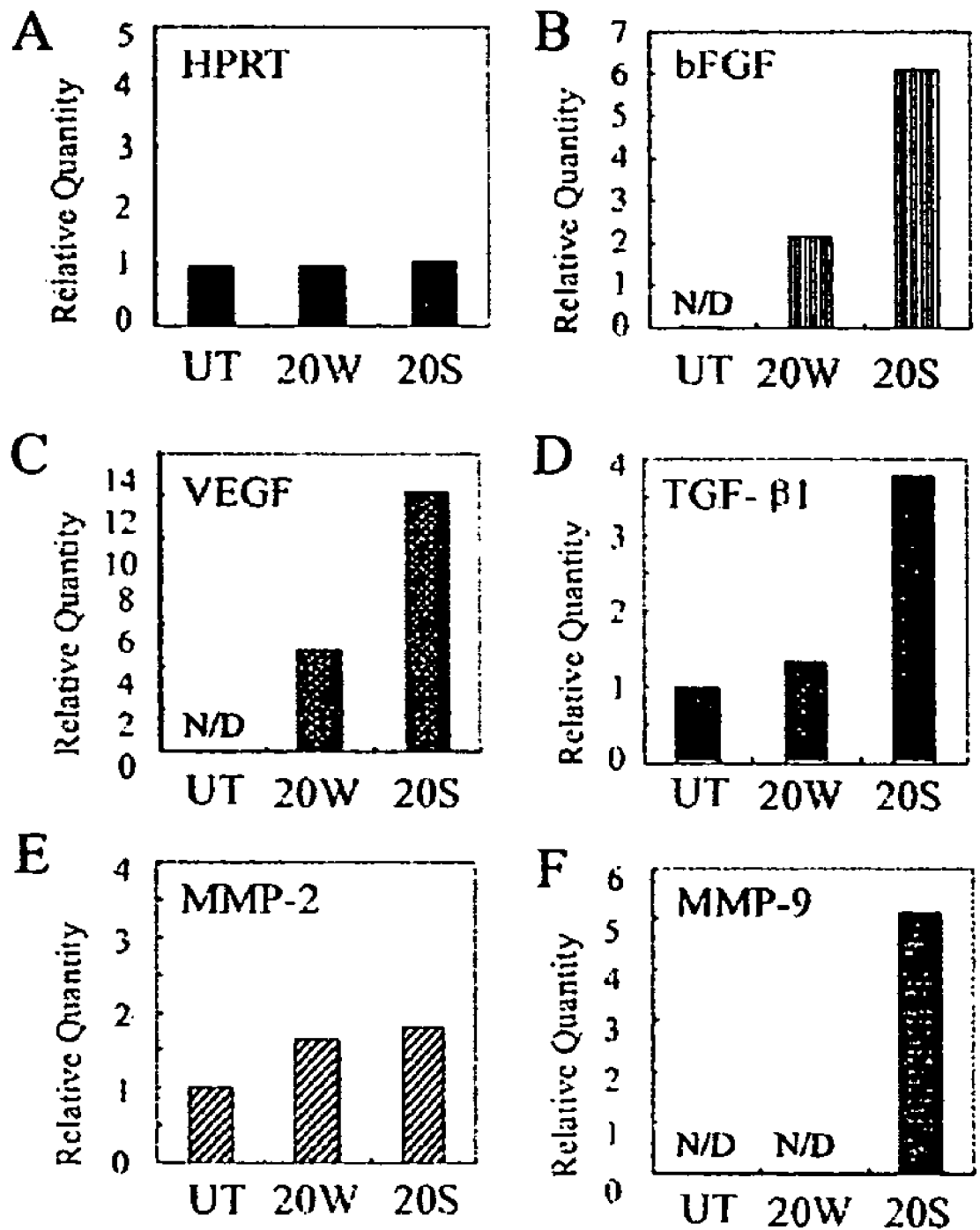

FIG. 5. Upregulation of bFGF, VEGF, TGF-β1, MMP-2, and MMP-9 transcripts by human (h)IL-20 on calf pulmonary artery endothelial cells (CPAEs).

CPAEs were incubated with either hIL-20 wild-type (500 ng/ml) or hIL-20 short-form (100 ng/ml) for 4 hours. Total RNA was isolated from CPAEs and underwent RT-PCR with random primer to make cDNA. Equal amounts of cDNA and primers specific for bFGF, VEGF, TGF-β1, MMP-2, and MMP-9 were used in PCR to amplify the transcripts. Primer specific for HPRT was used as an internal control. Amplified PCR fragments were run on agarose gel and stained with ethidium bromide. The relative quantity of PCR products was analyzed using the BIO-PROFIL program and expressed as a fold-increase relative to untreated control cells. N/D, no detectable transcript.

Figure 6:
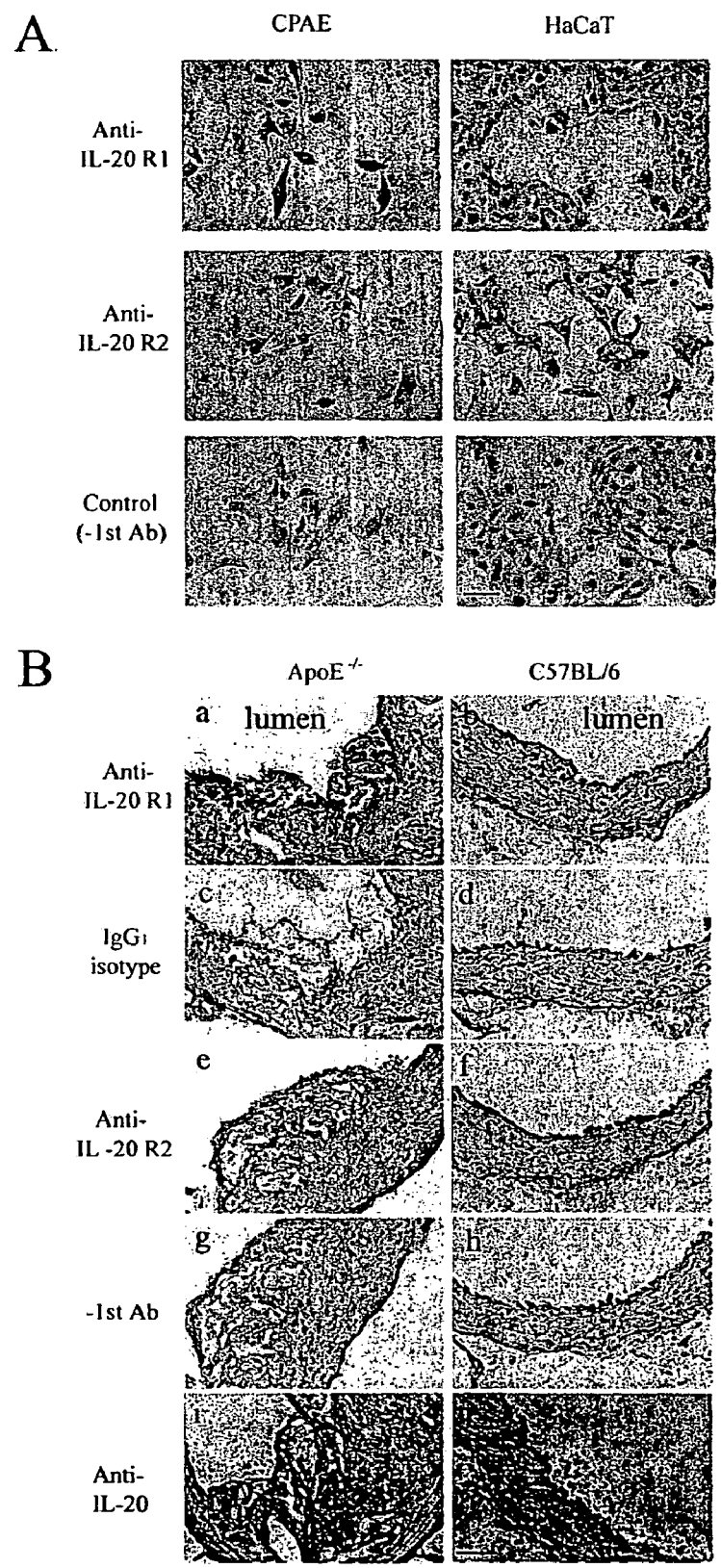

FIG. 6. Immunohistochemical staining of IL-20R1 and IL-20R2 in cultured calf pulmonary artery endothelial cells (CPAEs) and detection of IL-20 and receptor subunits in the aortic arch of 24-week-old ApoE$^{-/-}$ and normal C57BL/6 mice.

For cell staining, IL-20R1 expression was detected with mouse anti-human (h)IL-20R1 monoclonal antibody. IL-20R2 expression was detected with rabbit anti-hIL-20R2 polyclonal antibody. Staining with the secondary antibody alone served as the negative control. (A) Cultured CPAEs displayed positive staining of both IL-20R1 and IL-20R2. Positive control was performed on human keratinocyte HaCaT cells. (B) Detection of IL-20, IL-20R1, and IL-20R2 on aorta-section staining. IL-20R1 expression was detected with the mouse anti-hIL-20R1 monoclonal antibody using a Vector M.O.M. Peroxidase Kit (Ba-b). Staining with mouse IgGI isotype was used as the negative control (Bc-d). IL-20R2 expression was detected with rabbit anti-hIL-20R2 polyclonal antibody (Be-f). Staining with secondary antibody alone was used as the negative control (Bg-h). IL-20 expression was detected with rat anti-mouse IL-20 monoclonal antibody (Bi-j). Reactions were detected by DAB (brown), and nuclei were counterstained with hematoxylin (blue). Intensive staining for both receptor subunits and IL-20 ligand was observed in the aortic sections of ApoE$^{-/-}$ mice (Ba,e,i), while levels of IL-20R1, IL-20R2, and IL-20 (Bb,f,j) in the aortic sections of normal C57BL/6 mice were undetectable to low. Bars represent 50 μm (A) and (B).

Figure 7:
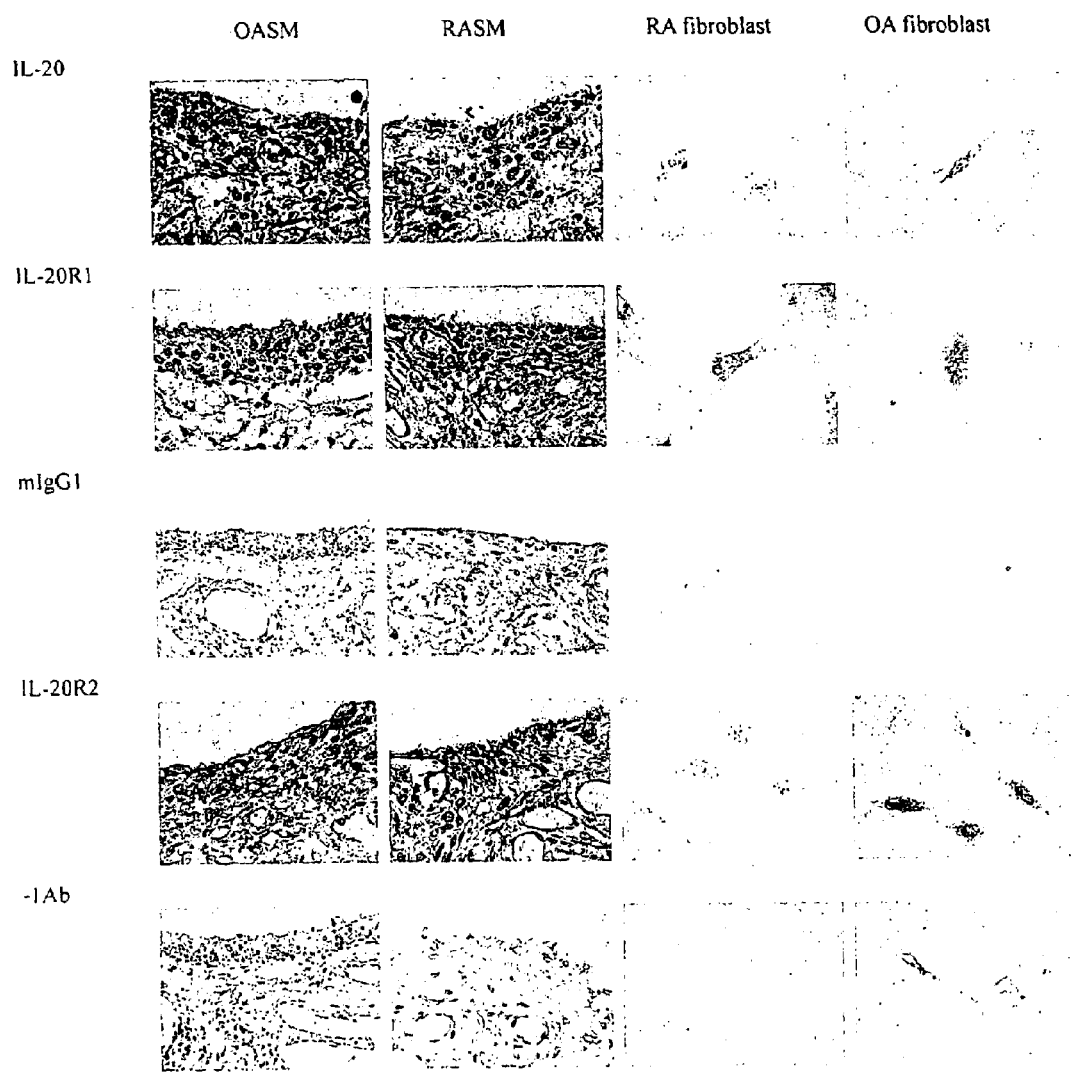

FIG. 7 Levels of IL-20 in Synovial Fluids of Patients with Rheumatoid Arthritis and Osteoarthritis.

Synovial fluid was collected from RA (n=) and OA (n=) patients and the levels of IL-20 in the synovial fluid from these two groups of patients were measured by ELISA.

Figure 8:
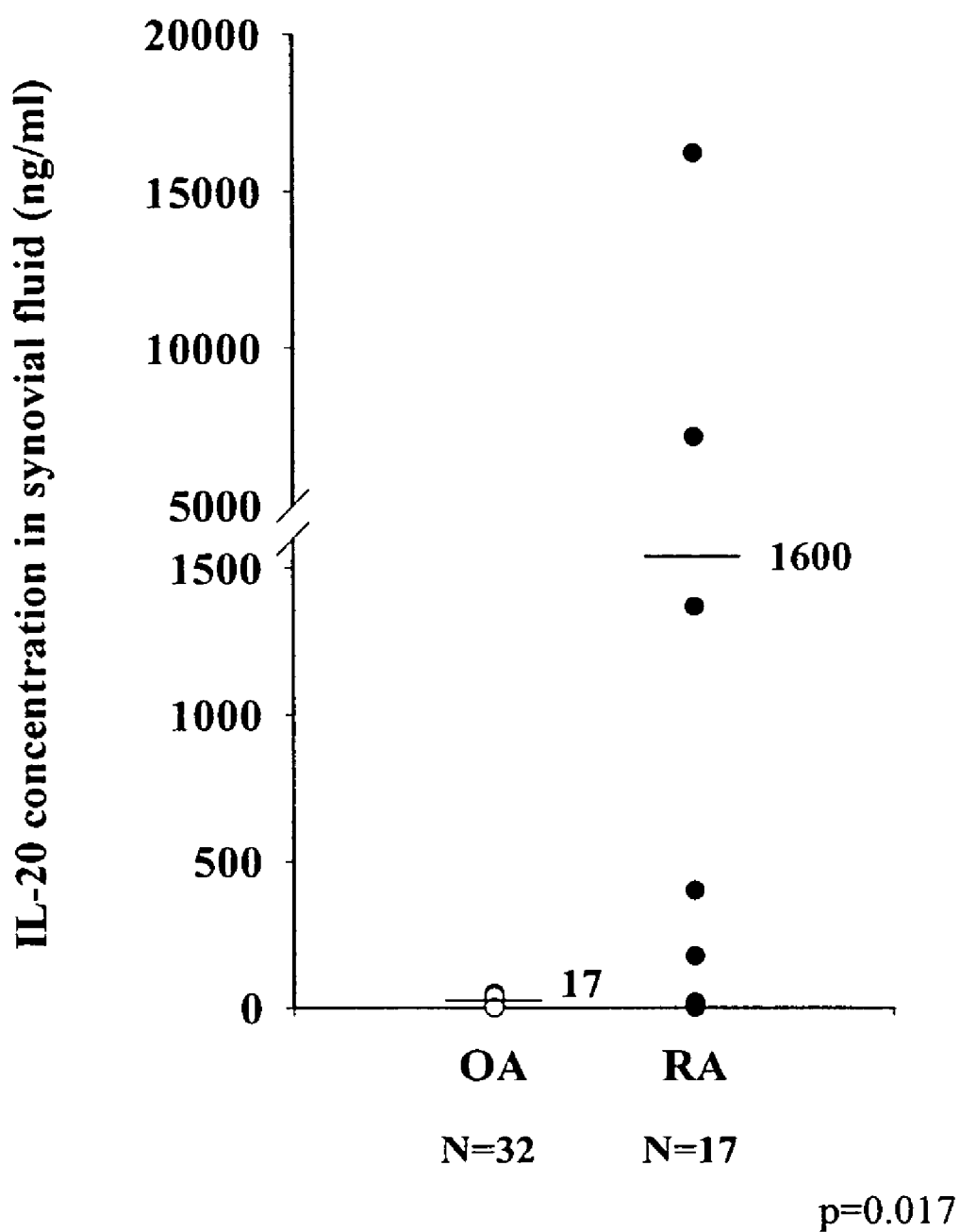

FIG. 8 Immunohistochemical staining of synovial membranes (SM) and synovial fibraoblast (SF) from OA and RA patients. Both IL-20 and IL-20 receptors were expressed in SM and SF of OA and RA patients.

DETAILED DESCRIPTION OF THE PRESENTLY PREFERRED EMBODIMENTS

Interleukin (IL)-10, an immunosuppressive cytokine, inhibits angiogenesis by downregulating vascular endothelial growth factor (VEGF) and attenuates atherosclerosis by downregulating metalloproteinase. IL-20 belongs to the IL-10 family and is involved in the pathogenesis of keratinocyte proliferation in vivo. To determine whether IL-20 acts on target cells other than keratinocytes, we treated calf pulmonary artery endothelial cells (CPAEs) with human IL-20 and analyzed its effect on the proliferation of the endothelial cells. We demonstrated that IL-20 induced proliferation of endothelial cells at concentrations from 25 to 500 nglml. Anti-human-IL-20 monoclonal antibody and soluble (s)IL-20 receptor (R)1 and sIL-20R2 completely blocked IL-20-induced proliferation. We also isolated an alternatively-spliced transcript of IL-20 from human cDNA libraries. Exon 4 was deleted in the human short-form of IL-20. The alternatively-spliced variant also induced proliferation of CPAEs. Furthermore, when optimal concentrations of IL-10 and IL-20 were co-incubated with endothelial cells, IL-10 diminished IL-20-induced proliferation of CPAEs. Incubation of IL-20 with CPAEs also induced transcripts of VEGF, TGF-β, and MMP-9. Both IL-20 and its receptor subunits, IL-20R1 and IL-20R2, were upregulated on endothelium and the atherosclerosis plaque in ApoE$^{-/-}$ mice. We demonstrated that IL-20 is a growth factor for endothelial cells and may be involved in atherosclerosis.

The present study demonstrated that hIL-20 at concentrations between 25 ng/ml and 500 ng/ml induced proliferation of CPAEs, and that it inhibited proliferation at concentrations above 500 ng/ml. The inhibition was not due to an overgrowth of cells that induced cell death, because when a high concentration of IL-20 was incubated with only one-tenth the number of CPAEs used in our reported experiments, it still inhibited cell proliferation (data not shown). The mechanism of inhibition at higher concentrations of IL-20 remains to be explored. Human IL-20s at the concentration of 12 ng/ml induced proliferation of CPAEs up to 200%, while hIL-20W at the concentration of 250 ng/ml induced proliferation up to 200%; thus, hIL-20s seems to be a more potent inducer of proliferation than hIL-20W. Commercially available hIL-20W protein (R&D Systems Inc.) derived from mammalian cells also showed lower activity than our hIL-20s at the same dose (data not shown). Our *E. coli*-derived hIL-20W protein showed the same potency as commercial hIL-20W protein derived from mammalian cells. Thus, the potency may not be due to the expression system of the recombinant proteins. Exon 4 was spliced out in hIL-20s. The detailed crystallographic structure of IL-20 remains unidentified to date, but the structures of the genes that encode members of the IL-10 family are expected to be highly conserved. The members of the hIL-10 family all have similar exon-intron structures. 16 Exon 4 encodes the DE loop and the E helix is spliced out in the short-form of hIL-20. The receptor-ligand complexes formed by the wild-type or short-form may recruit different molecules into intracellular signaling complexes. Alternatively, the binding affinity between the receptor and the ligand (wild-type or short-form) may be different. Further analysis of the Kd of these two forms is necessary to clarify their different activities.

Monoclonal antibody 7E, raised against ha-20W, completely neutralized the latter's proliferation activity, thereby demonstrating that the activity is specific. It only partially neutralized hIL-20s even at higher concentration (1 µg/ml), however. This may be attributed to differences in epitope recognition between these two forms. In addition, sIL-20R1 and sIL-20R2 completely blocked the proliferation activity of both hIL-20W and hIL-20S, further demonstrating that hIL-20-induced proliferation was specific. In Pletnev et al, IL-20 formed a stable ternary 1:1:1 complex with sIL-20R1 and sIL-20R2, as well as high-affinity binary complexes with sIL-20R2. However, both Pletnev et al and Parrish-Novak et al indicated that sIL-20R2 inhibited IL-19 activity but had no effect on IL-20 activity in their STAT-luciferase-activity assay. Our data showed that either sIL-20R1 or sIL-20R2 alone inhibited IL-20-induced proliferation. This discrepancy could be due to different assay systems.

Our results demonstrated that IL-20 may be a potent angiogenic factor. However, IL-24, another member of IL-10 family, exhibits its anti-angiogenic effect through IL-22R1 signaling. Thus, IL-20-induced proliferation might not signal through IL-22R1. Further study of the regulation of the ligand/receptor system should shed light on the molecular mechanisms of the different biological functions of these systems.

IL-10 at the concentration of 50-100 ng/ml induces cell death of endothelial cells. Our data demonstrated that IL-10 antagonized IL-20-induced proliferation. Because IL-10 and IL-20 do not share common receptors, however, they may compete for intracellular molecules for signal transduction. Alternatively, they antagonize each other by promoting or inhibiting specific angiogenesis factors. IL-10 downregulated the production of VEGF, MMP-2, and MMP-9. In contrast, hIL-20 upregulated the production of VEGF, TGF-$\beta$1, and MMP-9. These data indicated that IL-20 and IL-10 may have Yin and Yang effects on endothelial cells. IL-10 is an anti-angiogenesis factor and inhibits tumor metastasis; thus, IL-20 might be an angiogenesis factor and promote tumor metastasis.

MMP-9 is involved in atherogenesis and atherosclerosis plaque growth. Our data demonstrated that hIL-20S induced MMP-9 transcript in CPAEs but that hL-20W did not, which indicates that hIL-20S may play a crucial role in atherogenesis or atherosclerosis plaque growth. Therefore, the monoclonal antibody raised specifically against hIL-20S may serve as a therapeutic drug for the disease.

Our IHC staining showed that rabbit polyclonal antibody against hIL-20R2 recognized both bovine receptor (CPAEs) and mouse receptor (aorta endothelial cells). Similarly, mouse monoclonal antibody against hIL-20R1 recognized both bovine and mouse receptors. These data indicated that these two receptor subunits might share significant homology in the functional domain between these three species. Computer analysis of these two receptor subunits demonstrated that bovine IL-20R1 and IL-20R2 (partial EST sequence in NCBI database with accession numbers CK970095 and CN787148) share 65% and 72% homology with hIL-20R1 and hIL-20R2, while mIL-20R1 and mIL-20R2 share 78% and 72% homology with human receptors.

Atherosclerosis is a chronic vasculo-occlusive disease characterized by the intimal accumulation of macrophages, smooth muscle cells, and T lymphocytes, in addition to lipids and extracellular matrix components. Initiation and progression of atherosclerosis are dependent on an inflammatory intimal environment. Pro-inflammatory cytokines, including IL-1$\beta$, IL-6, IL-8, IL-12, TNF-$\alpha$, and interferon-$\gamma$, play a pivotal role in perpetuating this environment. Our data demonstrated that IL-20R1 and IL-20R2 were upregulated in the endothelium and plaque of atherosclerosis, suggesting that IL-20 may be involved in the process of atherosclerosis. Atherosclerosis plaque contains macrophages, T cells, and smooth muscles cells. It was not clear from IHC staining which cells expressed these two receptor subunits. However, we found that IL-20 also induced TNF-$\alpha$ and IL-6 production by CD8+ T cells (unpublished data). Therefore, it is possible that the T cells in atherosclerosis plaque expressed IL-20R1 and IL-20R2. Activation of monocytes by LPS and GM-CSF also induced production of IL-20. Therefore, we speculate that activated macrophages and T lymphocytes are the principal sources of proinflammatory cytokines that contribute to the formation of plaque, and that IL-20 plays a critical role in this process. Thus, deactivation of IL-20 may constitute an attractive new strategy for the prevention of atherosclerosis. Our monoclonal antibody, 7E, which completely neutralized hIL-20W, may have therapeutic potential. Furthermore, future development of the monoclonal antibody specific for hIL20S may be useful for the prevention or treatment of atherosclerosis because hIL-20s specifically upregulated MMP-9.

Cytokines represent a diverse group of molecules that collectively exert a wide range of actions. Recent discoveries showed that IL-20 targeted various cell types, such as keratinocytes and hematopoietic progenitor cells. Our data demonstrated that IL-20 also acted on endothelial cells as well as on CD8+ T cells. Thus, IL-20 is a pleiotropic cytokine and involved in inflammatory diseases and angiogenesis-associated diseases.

In summary, we demonstrated that IL-20 is a proliferation factor for endothelial cells and that it induced the expression of several angiogenesis factors, including VEGF, TGF-P, and MMP-9. We also discovered that IL-20 was associated with atherosclerosis because both the ligand and its receptor subunits were upregulated in endothelium and atherosclerosis plaque in A~OE−/−mice.

Isolation of hIL-20 Splice Variant

Figure 1:
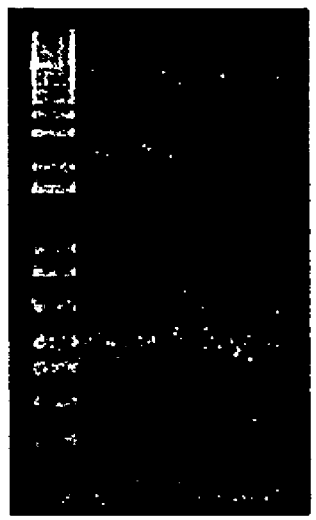
FIG. 1. Tissue distribution of two alternative-spliced transcripts of the human QIL-20 gene.

We used a pair of hL20-specific primers to amplify hIL-20 transcript on a panel of human cDNA libraries (kidney, lung, spleen, lymph node, thymus, bone marrow, brain, fetal liver, placenta, heart, testis, liver, and small intestine). PCR analysis showed that hIL-20 has two different transcripts. One is identical to what was reported (accession number AF224266) and named "wild-type" (hIL-20W). The other, a shorter transcript variant, was named "short-form". The wild-type is expressed in kidney, lung, and placenta tissues. The alternatively-spliced variant (short-form, hIL-20S) was found in lung tissue only (FIG. 1A). The hIL-20 gene was predicted to contain five exons and four introns. Exon 4 was deleted in the hIL20 short-form (FIG. 1B).

IL-20 Induced Proliferation of CPAEs

IL-10 is a pleiotropic cytokine with both pro- and anti-inflammatory effects in many cell lines. Therefore, we expressed and purified recombinant protein of hIL-20W and hIL-20S from *E. coli* and explored whether hIL-20 affected target cells other than keratinocytes. We treated CPAEs with either hIL-20W or hIL-20S and analyzed their effect on endothelial cell proliferation. We used bFGF (10 ng/ml) as a positive control. Human IL-20W induced proliferation of CPAEs at a concentration between 25 ng/ml and 1000 ng/ml, while hIL-20S induced proliferation of CPAEs at a concentration between 12 ng/ml and 100 ng/ml (FIG. 2A-B). However, incubation of CPAEs with a higher concentration of hIL-20 inhibited the proliferation of CPAEs. Human IL-20W inhibited proliferation of CPAEs at a concentration above 1000 ng/ml, while hIL-20S inhibited proliferation at a concentration higher than 200 ng/ml.

Anti-hIL-20 Monoclonal Antibodies Neutralized hIL-20-Induced Proliferation of CPAEs In order to confirm the specificity of IL-20-induced proliferation of CPAEs, we used the anti-hIL-20 monoclonal antibody, 7E, to neutralize hIL-20. When 7E alone was added to the culture, proliferation of CPAEs was not affected (FIG. 2C-D). However, 7E blocked hIL-20W-induced proliferation of CPAEs but did not block hIL-20s as potently. This could be attributed to a difference in the epitope recognition or binding affinity of 7E to hIL-20s because 7E was derived from hIL-20W antigen, not hIL-20S antigen.

sIL-20R1 and sIL-20R2 Inhibited IL-20-Induced Proliferation of CPAEs

IL-20 transduces its signal through the heterodimer receptor complex IL-20R1 and IL-20R2. We constructed sIL-20R1 and sIL-20R2 cDNA by cloning the extracellular domain of the receptors to analyze whether the soluble cytokine receptors block IL-20 activity. The optimal concentration of hIL-20W (250 ng/ml) or hIL-20S (100 ng/ml) was incubated at 4° C. for 30 minutes with sIL-20R1 before treating the CPAEs with it. Soluble IL-20R1 alone had no effect on CPAEs. Prior incubation of hIL-20W or hIL-20S with sIL-20R1 abolished IL-20-induced proliferation (FIG. 3A). Similarly, sIL-20R2 also inhibited IL-20-induced CPAE proliferation (FIG. 3B).

Interaction of IL-20 and IL-10

IL-10 is a potent anti-inflammatory cytokine that inhibits the release of TNF-α, IL-1, IL-6, and IL-8 in monocytes, macrophages, and neutrophils. IL-10 also blocks VEGF and FGF-2-induced proliferation of microvascular endothelial cells in vitro. These observations suggest a potent role for IL-10 in the prevention of angiogenesis. With the paradigm of the inflammatory nature of atherogenesis, we speculate that IL-10 may antagonize IL-20-induced proliferation. Various concentrations of IL-10 were added to the optimal concentration of hIL-20W (500 ng/ml) or hIL-20S (100 ng/ml) and co-incubated with CPAEs. IL-10 at a concentration of 25 ng/ml antagonized hIL20W- and hIL-20S-induced proliferation (FIG. 4).

Effects of IL-20 on Induction of Angiogenesis Factors

IL-10 can inhibit the generation of new vessels within a tumor both directly on tumor cells and indirectly by influencing infiltrating immune cells. IL-10 reduced the secretion of MMP-2 and MMP-9 from prostate cancer cells. Consequently, microvessel formation was inhibited. IL-10 downregulates MMP-2 to block tumor growth, angiogenesis, and metastasis, and TGF-P1 upregulates MMP-2 to stimulate tumor growth, angiogenesis, and metastasis. Because IL-10 downregulates several factors associated with angiogenesis, and IL-20 increases the proliferation of endothelial cells, we speculate that IL-20 may upregulate angiogenesis factors. Therefore, we treated CPAEs with hIL-20 and analyzed the transcripts of several angiogenesis factors: bFGF, TGF-β1, VEGF, MMP-2, and MMP-9. Bovine HPRT transcript was used as an internal control. Human IL20 upregulated the transcriptional levels of bFGF, VEGF, TGF-β1, and MMP-9 (FIG. 5; Table 2).

TABLE 2

Induction of bFGF, VEGF, TGF-PI, MMP-2, and MMP-9 transcripts on calf pulmonary artery endothelial cells (CPAEs) by human (h)IL-20

|  | BFGF | VEGF | TGF-b1 | MMP-2 | MMP-9 |
| --- | --- | --- | --- | --- | --- |
| Untreated | − | − | + | + | − |
| hIL-20W | + | + | + | + | − |
| hIL-20S | + | ++ | ++ | + | ++ | bFGF indicates basic fibroblast growth factor;
VEGF, vascular endothelial growth factor;
TGF-β1, transforming growth factor-beta-1;
MMP, matrix metalloproteinase;
hIL-20, human interleukin-20;
−, no detectable transcript;
+ and ++, levels of detectable expression;
W, wild-type;
S, short-form.

Detection of IL-20R Subunits on CPAEs Using IHC Staining

To confirm the expression of IL-20 receptors on endothelial cells, immunostaining of both IL-20R1 and IL-20R2 was performed on CPAEs using antibody against hIL-20R1 and hIL-20R2 subunits. Strong immunoreactivity was detected for IL-20R1 in CPAEs, whereas moderate immunoreactivity was detected for hIL-20R2 (FIG. 6A). HaCaT cells, the positive control, exhibited moderate immunoreactivity toward both hIL-20R1 and hIL-20R2. This result indicated that human and bovine IL-20 receptors may share significant homology and that hIL-20 acted across species on bovine cells. These results demonstrated that endothelial cells expressed functional receptor subunits for IL-20.

Upregulation of Both IL-20 and its Receptors in Atherosclerosis Lesions

Proliferation of endothelial cells plays a crucial role in atherosclerosis. IL-20 induced proliferation of endothelial cells. Furthermore, chronic inflammation plays a pivotal role in the progression of atherosclerosis. IL-10 exerts important protective effects against the development of atherosclerosis lesions in experimental animals. Therefore, we wanted to see whether IL-20 also played some role in atherosclerosis. ApoE-knockout mice demonstrate the atherosclerosis phenotype. Thus, we used antibodies against IL-20 or its receptors in immunostaining to analyze the expression of the ligand or the receptors in the atherosclerosis lesion in 24-week-old ApoE$^{-/-}$ atherosclerotic mice. We found that IL-20 was upregulated in the atherosclerosis plaque of ApoE-deficient mice (FIG. 6Bi-j). To examine whether the expression of IL-20 receptors is also altered in atherosclerosis lesions, immunostaining of IL-20RI and IL-20R2 was performed in cryosections of the aortic arches of ApoE$^{-/-}$ mice and normal C57BL/6 mice. In the aortic arches of normal C57BL/6 mice, low levels of IL-20R1 and IL-20R2 were detected in a portion of the endothelial cells (FIG. 6Bb,f). In contrast, strong immunoreactivity was detected for both IL-20R1 (FIG. 6Ba) and IL-20R2 (FIG. 6Be) in the endothelium of the aortic arches of ApoE$^{-/-}$ mice. In addition, intensive staining of IL-20R1 and IL-20R2 was detected in atherosclerosis plaque. Immunoreactivity was detected in the adventitia of the aortic arches of both C57BL/6 and ApoE$^{-/-}$ mice. These results indicated that both IL-20 and IL-20 receptors are induced in atherosclerosis plaque and are markedly upregulated in the endothelium of atherosclerotic aortas.

Treatment of Rheumatoid Arthritis

Rheumatoid arthritis (RA) is a common chronic inflammatory polyarthritis of worldwide distribution, with a female predomaince of 3:1 and a peak onset in the fourth decade of life. Intense inflammation occurs in synovial joints, so that the normally delicate synovail "membrane" becomes infiltrated with mononclear phagocytes, lyphocytes, and neutrophils. An inflammatory fluid is usually exuded by the inflamed synovium. In addition to pain and loss of mobility of joints patients frequently develop systemic manifestation, such as anemia, subcutaneous of manifestation nodules, pleurisy, pericarditis, interstitial lung disease, and manifestation of vasculitis such as nerve infarction, skin lesion, and inflammation of the ocular sclera. The course of RA is variable, but usually patients undergo progressive loss of cartilage and bone around joints with resulting diminished mobility.

Although the course of RA remains unknown, a number of its features are suggestive of an autoimmune etiology. The pathology of arthritic joints suggests a T-cell-mediated chronic inflammatory reaction. Most patients (over 80%) develop antibody in their blood called IgM rheumatoid factor RF, mostly produced in the marrow, but with significant production by the inflamed synovium. The presence of intrasynovial immune complex, together with diminished levels of complement components, implies an involvement of RF in some of the local pathology. In recent years, however, much interest has focused on the T cell and mononuclear phagocytes infiltrating the joint. T cells are probably polyclonal, although evidence for selective expansion of certain Vβ subsets exists and has led some investigators to propose a role for superantigens. Depletion of T cells by thoracic duct drainage, or by immunosuppressive drugs such as cyclosporine, has resulted in improvement, implying an important role for T cells in the inflammatory process. Much work on intrasynovial cytokines, however, has pointed toward mononuclear phagocytes as the prime driving force of the inflammatory process.

The synovial fluid in RA contains primarily cytokines of mononuclear origin, including IL-1, IL-6 and TNF-α. IL-1 receptor antagonist can also be demonstrated in most fluids. In contrast, IL-2, IFN-v, and other T-cell cytokines are usually present in only small quantities, with the possible exception of IL-17. Efforts to treat RA with T-cell-depleting monoclonal antibodies have yielded disappointing results. In contrast, administration of monoclonal antibodies to TNF-α has resulted in marked reduction of inflammation. Modest improvement has also been reported for antibodies to IL-6 and with administration of IL-1 receptor antagonist.

The mechanism whereby joint inflammation results in crippling cartilage and bone erosion in RA is incompletely understood. It seems unlikely that leakage into cartilage of neutrophil or mononuclear phagocyte-derived proteolytic enzymes is responsible. The diffusion through the cartilage matrix of cytokines probably stimulates breakdown of cartilage and bone through an action on chondrocytes and osteoclasts. In this regard, the TNF-family cytokine RANK ligand (RANKL) appears to be of particular importance, as overexpression of RANKL and its receptor predispose to erosive arthritis in the collagen model, and lack of RANKL allows induction of arthritis yet prevents cartilaginous and bony destruction. Currently, Enbrel is the commercial drug and used to treat RA to reduce inflammation of joints. Enbrel is the soluble receptor of TNA-α.

This invention discloses that IL-20 is upregulated in the synovial fluid of RA joints. (FIG. 7). Synovial membrane and the fibroblast derived from synovial membrane also expressed receptors for IL-20, IL-20 R1 and IL-20 R2. (FIG. 8) Thus, IL-20 may play a crucial role in pathogenesis of RA. Our previous discovery also disclosed that IL-20 induced TNF-α production from monocytes and T cells. Therefore, a molecule to block activity of IL-20 should block activity of TNF-α. The IL-20 monoclonal antibody, 7E, demonstrated full activity to inhibit IL-20 activity. This antibody will have therapeutic potential to treat RA and atherosclerosis or any other inflammatory disease associated with IL-20.

The invention is not limited by the embodiments described above which are presented as examples only but can be modified in various ways within the scope of protection defined by the appended patent claims.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

The following examples further illustrate the present invention and should not be deemed as limitation of the scope of the present invention.

EXAMPLE 1

Materials and Methods for Isolation of hIL-20 Spliced Variants

We used a pair of primers on exon 1

```
                                              (SEQ ID NO: 3)
(sense primer: 5'-CTCCAGATTTCAGGCCTAAGATG-3')
``` and exon 5

(antisense primer: 5'-ATTGAAGACTGGAGCTCT-TGACC-3') (SEQ ID NO: 4) in PCR amplification to detect the short-form transcript on a panel of human cDNA libraries (Clontech, Inc., Palo Alto, Calif.).

EXAMPLE 2

Cell Culture

CPAEs purchased from ATCC (American Type Culture Collection) were grown in MEM with 20% fetal bovine serum and 1% penicillin/streptomycin in a humidified atmosphere with 5% $CO_2$ at 37° C. Cultures were dissociated with 0.1% trypsin. Cells between passages 19 and 25 were used for experiments.

EXAMPLE 3

Expression and Purification of Recombinant hIL-20

Both wild-type (W) and short-form (S) hIL-20 were expressed in *E. coli*. A cDNA-clone coded for the hIL-20 sequences from leucine to leucine (amino acid 25 to amino acid 176) was inserted into pET43*a* (Novagen, Madison, Wis.). The protein was found mostly in the cytosol and was purified to more than 95% using an affinity chromatography series.

EXAMPLE 4

Generation of IL-20 Monoclonal Antibody

BALB/cJ mice were immunized subcutaneously every week for 4 weeks with recombinant hIL-20 protein (100 .mu.g/mouse) emulsified with an equal volume of Freund's complete/incomplete adjuvant. Three days before fusion, three mice were boosted by intravenous injection of the antigen without adjuvant. Spleen cells (1.2.times.10.sup.8) from immunized mice were fused with X63-Ag8-6.5.3 myeloma cells (1.5.times.10.sup.7) with PEG 4000 (Merck & Co., Inc., Whitehouse Station, N.J.). After fusion, the cells were distributed into 24-well plates and cultured in HAT medium for 14 days. Using ELISA, culture supernatant was tested for antibody reacting with hIL-20. To clone the selected hybridoma cell, the limiting dilution was carried out twice. The hybridoma cells were cultured in Dulbecco's Modified Eagle's medium (GIBCO; Invitrogen Corporation, Carlsbad, Calif.) containing 15% fetal calf serum, 1% penicillin/streptomycin, 2% L-glutamine, and 1% adjusted NaHC0.sub.3 solution. The isotype of the selected antibody, IgG, was determined using isotyping ELISA. The antibody was purified from ascites using Protein-A chromatography. The hybridoma producing anti hIL-20 monoclonal antibody 7E is deposited on Oct. 16, 2007 at the American Type Culture Collection, 10801 University Boulevard, Manassas, Va. 20110-2209, U.S.A. and has been assigned a deposit number PTA-8687.

EXAMPLE 5

Expression and Purification of the Extracellular Domains of hIL-20R1 and hIL-20R2 Recombinant Protein RNA was isolated from HaCaT cells and reverse transcribed into cDNA. The extracellular domain of IL-20R1 was amplified with PCR using the sense primer

```
5'-AGCGAATTCGTTCCCTGTGTCTCTGGT-3'  (SEQ ID NO: 5)
``` and the antisense primer

```
5'-TTI'AGCC'ITGAACTCTGATG-3'.  (SEQ ID NO: 6)
```

The amplified PCR fragment coding from Val to Lys (aa 30-250) was inserted into the *E. coli* expression vector of pMAL-c2X (NEB, Beverly, Mass.).

The extracellular domain of IL-20R2 was amplified with PCR using the sense primer

```
5'-TGGCTGAGATGGACAGAATG-3'  (SEQ ID NO: 7)
``` and the antisense primer

```
5'-CCTTCCGCAAACCTATGAGA-3'.  (SEQ ID NO: 8)
```

The amplified PCR fragment coding from Asp to Pro (aa 30-232) was inserted into the expression vector of *Pichia pastoris* (pPICZ-αA; Invitrogen, Inc., San Diego, Calif.). An expression Taq consisting of six histidine residues was placed at the C-terminus of the recombinant proteins. IL-20R1 extracellular domain protein was expressed and purified from the cytosol of bacteria cells. IL-20R2 extracellular domain protein was expressed and purified from the culture media of the yeast cells using metal affinity chromatography, which yielded 1-2 mg of pure protein/L of conditioned media. This protein was used in biological function analysis in vitro and for the generation of polyclonal antibody (described in the following paragraph).

EXAMPLE 6 hIL-20R1 and hIL-20R2 Antibodies and Mouse IL-20 Antibody

Commercially available mouse IL-20 antibody (clone 176005; R&D Systems, Minneapolis, Minn.) and hIL-20R1 monoclonal antibody characterized as able to recognize both human and mouse IL-20R1 (clone 173707; R&D Systems, Minneapolis, Minn.) were used in immunohistochemical staining. IL-20R2 polyclonal antibody was generated by immunizing rabbits with the human soluble (s)IL-20R2 extracellular domain following the standard protocol. The polyclonal antibody was purified using protein-A affinity chromatography.

EXAMPLE 7

Cell Proliferation Assay

CPAEs were plated in 24-well plates at a density of $1\times10^4$ cells per well. After 24 hours of incubation in normal growth medium, cells were exposed to various concentrations of wild-type hIL-20 or short-form hIL-20 for 72 hours. Cells were then incubated with a 1-mg/ml solution of 3-[4,5-Dimethylthiazol-2-yl]-2,5-diphenyltetrazolium bromide (MTT) (Sigma, St. Louis, Mo.) for 4 hours. Two hundred pl of DMSO (Dimethyl Sulfoxide) (Sigma) was added to the culture. Absorbance of 550 nm was determined using an ELISA reader. The absorbance of cytokine-treated cells was expressed as a percentage of untreated control cells. Basic fibroblast growth factor (bFGF) (Sigma) was used as the positive control in the cell proliferation assay.

EXAMPLE 8

Neutralization of IL-20 Activity by Monoclonal Antibody or Receptors

CPAEs were seeded at a density of $1\times10^4$ cells per well in 24-well plates for 24 hours at 37° C. Before treatment, 10-folds excess of anti-hIL-20 monoclonal antibody 7E or sIL-20R1 or sIL-20R2 protein were incubated with an optimal concentration of hIL-20S (100 ng/ml) or hIL-20W (250 ng/ml) for 30 minutes at 4° C. The mixtures of IL-20 with 7E or IL-20 with sIL-20R1 or IL-20 with sIL-20R2 were added to the CPAEs and incubated for 72 hours. Cells were then incubated with 1 mg/ml MTT solution for 4 hours. Two hundred μl of DMSO was added to the culture. Absorbance of 550 nm was determined using an ELISA reader.

EXAMPLE 9

Detection of Induced Transcripts for Angiogenesis Factors Using RT-PCR

To investigate the transcription level of bFGF, VEGF, transforming growth factor (TGF)-PI, matrix metalloproteinase (MMP)-2, and MMP-9 on hIL-20-stimulated CPAEs, cells were seeded at a density of $5\times10^5$ cells per well into 6-well plates for 24 hours in MEM medium supplemented with 20% FBS. Culture cells were then exposed to hIL-20W (250 ng/ml) or hIL-20S (100 ng/ml) for 4 hours in serum-free MEM. Total RNA from hIL-20 stimulated CPAEs was extracted using RNAzol Bee reagent (Tel-Test, Inc., Friendswood, Tex.) following the manufacturer's instructions. Total RNA underwent reverse transcription in 20 μl of reaction volume using a random primer according to the protocol of the manufacturer (BD Biosciences, San Jose, Calif.). cDNA (1 μl) was used for further quantitative analysis. Each PCR was performed for 25 cycles (30 seconds at 94° C., 30 seconds at 62° C., 30 seconds at 72° C.). PCR products were visualized on 2% agarose gels containing ethidium bromide. Incubations in which cDNA was omitted were used as negative controls. The sequences of the bovine-specific PCR primers are given in Table 1. The relative quantity of PCR products was analyzed using the BIO-PROFIL program (Vilbert Lourmat, France).

TABLE 1

Primer pairs used for amplifying bovine transcripts (SEQ ID NOS 9-20, respectively in order of appearance)

| Factor | Primer sequence (5'-3') | Product size |
|---|---|---|
| HPRT | Forward-GAGATGTGATGAAGGAGATGG<br>Reverse CAGCAAGCTCGCAACCTTGA | 341-bp |
| bFGF | Forward-ACTTCAAGGACCCCAAGCGG<br>Reverse GCTTTCTGCCCAGGTCCTG | 361-bp |
| VEGF | Forward-GTGGTGAAGTTCATGGATGTC<br>Reverse CACGTCTGCGGATCTTGTAC | 365-bp |
| TGF-P1 | Forward-GAGCAGCACGTGGAGCTGTA<br>Reverse CGGCCCACGTAGTACACGAT | 621-bp |
| MMP-2 | Forward-CAAGGGTACAGCCTGTTCCT<br>Reverse TTCCCTGCAAAGAACACAGCC | 435-bp |
| MMP-9 | Forward--ACATCTTCGACGCCATCGCG<br>Reverse AACTCACGCGCCAGTAGAAG | 494-bp |

EXAMPLE 10

Immunocytochemical Staining of CPAEs

For immunocytochemical staining, CPAEs grown on plastic slides (Lab-Tek chamber slides; Electron Microscopy Sciences, Hatfield, Pa.) were washed twice in PBS and fixed in 4% paraformaldehyde for 10 minutes and permeabilized using PBS with 0.1% Triton X-100. Nonspecific binding sites were blocked by incubation in PBS/BSA (0.1% w/v) followed by incubation with primary antibodies (IL-20R1 monoclonal or DL-20R2 polyclonal antibody) for 1 hour at room temperature, and then incubation with the secondary antibody. For negative control, cells were incubated with only the secondary antibody without prior incubation with IL-20R1 or IL-20R1 to demonstrate the background.

EXAMPLE 11

Mice

C57BL/6 and ApoE$^{-/-}$ (The Jackson Laboratory, Bar Harbor, Me.) mice with the C57BL/6 genetic background were used throughout the study. Mice were fed a regular chow diet or the atherogenic diet (AD) contain 0.15% of cholesterol. 24-week-old mice were used in our study. All animal care and experimental procedures conformed to the regulations of the Committee of Cheng Kung University on Animal Experimentation. For immunohistochemical staining, hearts and ascending aortas of animals were fixed in formaldehyde, and serial 10-μm-thick cryosections were cut from the aortic arch to the ventricles for analysis of atherosclerosis.

EXAMPLE 12

Immunohistochemical Staining of Aortas from Atherosclerotic Mice

Frozen aortic arch sections from 24-week-old C57BL/6 normal mice and ApoE$^{-/-}$ mice were used for immunohistochemical staining. The sections were fixed in 4% paraformaldehyde and immersed in antibody diluent with background-reducing components (DakoCytomation, Carpinteria, Calif.)

for 60 minutes to suppress nonspecific immunoglobulin staining. The slides were soaked in 90 ml of methanol and 10 ml of 30% $H_2O_2$ for 10 minutes at room temperature to block endogenous peroxidases, washed with PBS, and then incubated with anti-hIL-20R2 rabbit-polyclonal antibody in blocking reagent at 4° C. overnight. The slides were then treated consecutively with HRP-conjugated goat anti-rabbit IgG (Biolegend, San Diego, Calif.) and incubated for 2 hours at room temperature. Slides were incubated with the diaminobenzidine DAB substrate kit (Vector Laboratories, Burlingame, Calif.) and counterstained with Mayer's hematoxylin (Thermoshandon, Pittsburgh, Pa.). Negative control without incubation with primary antibody was performed simultaneously. To stain IL-20R1, primary antibody (R&D Systems) was diluted to 150 using a staining kit (Vector M.O.M. Peroxidase Kit PK-2200; Vector Laboratories) and Vectastain Elite ABC reagent (included in the M.O.M. kit) according to the manufacturer's protocol. Mouse IgG1 isotype (clone 1171 1; R&D Systems) was used as a negative control for the primary antibody. HRP-conjugated goat anti-mouse IgG (Biolegend) was used as the secondary antibody to detect the signal of the primary antibody bound to the tissue. To stain mouse IL-20, primary antibody (clone 176005; R&D Systems) was diluted to 1:200 and detected with biotin-labeled rat anti-mouse IgG secondary antibody and ABC reagent.

EXAMPLE 13

Statistical Analysis

Significant difference was detected with Student's t test using a statistical software package in Microsoft Excel. Results are given as mean+SD (unless otherwise indicated), and statistical significance was set at $P<0.05$.

The following references are incorporated by reference in their entirety.
1. O'Farrell A M, Liu Y, Moore K W, Mui A L. IL-10 inhibits macrophage activation and proliferation by distinct signaling mechanisms: evidence for Stat3-dependent and —independent pathways. EMBO J. 1998; 17: 1006-1018.
2. Gesser B, Leffers H, Jinquan T, et al. Identification of functional domains on human interleukin 10. Proc Natl Acad Sci USA. 1997; 94:14620-14625.
3. Ding Y, Qin L, Kotenko S V, Pestka S, Bromberg J S. A single amino acid determines the immunostimulatory activity of interleukin 10. J Exp Med. 2000; 191:213-224.
4. Go N F, Castle B E, Barrett R, et al. Interleukin 10, a novel B cell stimulatory factor: unresponsiveness of X chromosome-linked immunodeficiency B cells. J Exp Med. 1990; 172:1625-1631.
5. Thompson-Snipes L, Dhar V, Bond M W, Mosmann T R, Morre K W, Rennick D M. Interleukin 10: a novel stimulatory factor for mast cells and their progenitors. J Exp Med. 1991; 173:507-510.
6. Rousset F, Garcia E, Defrance T, et al. Interleukin 10 is a potent growth and differentiation factor for activated human B lymphocytes. Proc Natl Acad Sci USA. 1992; 89: 1890-1893.
7. de Waal M R. Interleukin-10. In: Mire-Sluis A S, Thorpe R, eds. Cytokine. San Diego, Calif.: Academic Press; 1998: 151.
8. de Waal Malefyt R, Abrams J, Bennett B, et al. Interleukin 10(IL-10) inhibits cytokine synthesis by human monocytes: an autoregulatory role of IL-10 produced by monocytes. J Exp Med. 1991; 174:1209-1220.
9. Steams M E, Rhim J, Wang M. Interleukin 10 (IL-10) inhibition of primary human prostate cell-induced angiogenesis: IL-10 stimulation of tissue inhibitor of metalloproteinase-1 and inhibition of matrix metalloproteinase (MMP)-2/MMP-9 secretion. Clin Cancer Res. 1999; 5: 189-196.
10. Ross R. Atherosclerosis—An inflammatory disease. N Engl J Med. 1999; 340: 115-126.
11. van der Wal A C, Becker A E, van der Loos C M, Das P K. Site of intimal rupture or erosion of thrombosed coronary atherosclerotic plaques is characterized by an inflammatory process irrespective of the dominant plaque morphology. Circulation. 1994; 89:36-44.
12. Fuster V, Badimon L, Badimon J J, Chesebro J H. The pathogenesis of coronary artery disease and the acute coronary syndromes (1). N Engl J Med. 1992; 326:242-250.
13. Fuster V, Badimon L, Badimon J J, Chesebro J H. The pathogenesis of coronary artery disease and the acute coronary syndromes (2). N Engl J Med. 1992; 326:3 10-3 18.
14. Lee R T, Libby P. The unstable atheroma. Arterioscler Thromb Vasc Biol. 1997; 17: 1859-1867.
15. Mallat Z, Besnard S, Duriez M, et al Protective role of interleukin-10 in atherosclerosis. Circ Res. 1999; 85:e17-24.
16. Pestka S, Krause C D, Sarkar D, Walter M R, Shi Y, Fisher P B. Interleukin-10 and related cytokines and receptors. Annu Rev Immunol. 2004; 22:929-979.
17. Fickenscher H, Hor S, Kupers H, Knappe A, Wittrnann S, Sticht H. The interleukin-10 family of cytokines. Trends Immunol. 2002; 23:89-96.
18. Langer J A, Cutrone E C, Kotenko S V. The Class I1 cytokine receptor (CRF2) family: overview and patterns of receptor-ligand interactions. Cytokine Growth Factor Rev. 2004; 15:33-48.
19. Gallagher G Dickensheets H, Eskdale J, et al Cloning, expression and initial characterization of interleukin-19 (IL-19), a novel homologue of human interleukin-10 (IL-10). Genes Immun. 2000; 1:442-450.
20. Liao Y C, Liang W G, Chen F W, Hsu J H, Yang J J, Chang M S. IL-19 induces production of L-6 and TNF-alpha and results in cell apoptosis through TNF-alpha. J Immunol. 2002; 169~4288-4297.
21. Liao S C, Cheng Y C, Wang Y C, et al. Interleukin-19 induced Th2 cytokines and was up-regulated in asthma patients. J mmuno 1. 2004; 173 :6712-6718.
22. Wolk K, Kunz S, Asadullah K, Sabat R. Cutting edge: immune cells as sources and targets of the IL-10 family members? J Immunol. 2002; 168:5397-5402.
23. Blumberg H, Conklin D, Xu W F, et al. Interleukin 20: discovery, receptor identification, and role in epidermal function. Cell. 2001; 104:9-19.
24. Liu L, Ding C, Zeng W, et al. Selective enhancement of multipotential hematopoietic progenitors in vitro and in vivo by IL-20. Blood. 2003; 102:3206-3209.
25. Dumoutier L, Leemans C, Lejeune D, Kotenko S V, Renauld J C. Cutting edge: STAT activation by IL-19, IL-20 and mda-7 through IL-20 receptor complexes of two types. J Immunol. 2001; 167:3545-3549.
26. Dumoutier L, Van Roost E, Colau D, Renauld J C. Human interleukin-10-related T cell-derived inducible factor: molecular cloning and functional characterization as a hepatocyte-stimulating factor. Proc Natl Acad Sci USA. 2000; 97: 10144-10149.
27. Radaeva S, Sun R, Pan H N, Hong F, Gao B. Interleukin 22 (IL-22) plays a protective role in T cell-mediated murine hepatitis: IL-22 is a survival factor for hepatocytes via STAT3 activation. Hepatology. 2004; 39: 1332-1342.

28. Wolk K, Kunz S, Witte E, Friedrich M, Asadullah K, Sabat R. IL-22 increases the innate immunity of tissues. Immunity. 2004; 21:241-54.
29. Jiang H, Lin J J, Su Z Z, Goldstein N I, Fisher P B. Subtraction hybridization identifies a novel melanoma differentiation associated gene, mda-7, modulated during human melanoma differentiation, growth and progression. Oncogene. 1995; 11:2477-2486.
30. Knappe A, Hor S, Wittmann S, Fickenscher H. Induction of a novel cellular homolog of interleukin-10, AK155, by transformation of T lymphocytes with herpesvirus saimiri. J Virol. 2000; 74:3881-3887.
31. Hor S, Pirzer H, Dumoutier L, et al. The T-cell lymphokine interleukin-26 targets epithelial cells through the interleukin-20 receptor 1 and interleukin-10 receptor 2 chains. J Biol. Chem. 2004; 279:33343-33351.
32. Sheikh F, Baurin W, Lewis-Antes A, et al. Cutting edge: IL-26 signals through a novel receptor complex composed of IL-20 receptor 1 and IL-10 receptor 2. J Immunol. 2004; 172-2006-2010.
33. Plump A S, Smith J D, Hayek T, et al. Severe hypercholesterolemia and atherosclerosis in apolipoprotein E-deficient mice created by homologous recombination in ES cells. Cell. 1992; s 1:343-353.
34. Zhang S H, Reddick R L, Piedrahita J A, Maeda N. Spontaneous hypercholesterolemia and arterial lesions in mice lacking apolipoprotein E. Science 1992; 258:468-471.
35. Wang P, Wu P, Siegel M I, Egan R W, Billah M M. IL-10 inhibits transcription of cytokine genes in human peripheral blood mononuclear cells. J Immunol. 1994; 153: 811-816.
36. Fiorentino D F, Zlotnik A, Mosmann T R, Howard M, and O'Garra A. IL-10 inhibits cytokine production by activated macrophages. J Immunol. 1991; 147:3815-3822.
37. Cervenak L, Morbidelli L, Donati D, et al. Abolished angiogenicity and tumorigenicity of Burkitt lymphoma by interleukin-10. Blood. 2000; 96:2568-2573.
38. Stearns M E, Garcia F U, Fudge K, Rhim J, Wang M. Role of interleukin 10 and transforming growth factor beta1 in the angiogenesis and metastasis of human prostate primary tumor lines from orthotopic implants in severe combined immunodeficiency mice. Clinical Cancer Research 1999; 5:711-720.
39. Pletnev S, Magracheva E, Kozlov S, et al. Characterization of the recombinant extracellular domains of human interleukin-20 receptors and their complexes with interleukin-19 and interleukin-20. Biochemistry. 2003; 42: 12617-12624.
40. Parrish-Novak J, Xu W, Brender T, et al. Interleukins 19, 20, and 24 signal through two distinct receptor complexes. Differences in receptor-ligand interactions mediate unique biological functions. J Biol. Chem. 2002; 277:47517-23.
41. Ramesh R, Mhashilkar A M, Tanaka F, et al. Melanoma differentiation-associated gene 7linterleukin (1L)-24 is a novel ligand that regulates angiogenesis via the IL-22 receptor. Cancer Res. 2003; 63:5105-13.
42. Gimeno M J, Pascual G, Garcia-Honduvilla N, et al. Modulatory role of IL10 in endothelial cell damage and platelet adhesion. Histol Histopathol. 2003; 18:695-702.
43. Asadullah K, Sterry W, Volk H D. Interleukin-10 therapy—review of a new approach. Pharmacol Rev. 2003; 55:241-269.
44. Luttun A, Lutgens E, Manderveld A, et al. Loss of matrix metalloproteinase-9 or matrix metalloproteinase-12 protects apolipoprotein E-deficient mice against atherosclerotic media destruction but differentially affects plaque growth. Circulation. 2004; 109:1408-1414.
Ozaki K, Leonard W J. Cytokine and cytokine receptor pleiotropy and redundancy. J Biol Chem. 2002; 277: 29355-29358.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A monoclonal antibody produced by a hybridoma cell line deposited with the American Type Culture Collection as Deposit Number PTA-8687.

* * * * *

SEQUENCE LISTING

```
<160> NUMBER OF SEQ ID NOS: 20

<210> SEQ ID NO 1
<211> LENGTH: 175
<212> TYPE: PRT
<213> ORGANISM: Homo sapiens

<400> SEQUENCE: 1

Met Lys Ala Ser Ser Leu Ala Phe Ser Leu Leu Ser Ala Ala Phe Tyr
 1               5                  10                  15

Leu Leu Trp Thr Pro Ser Thr Gly Leu Lys Thr Leu Asn Leu Gly Ser
            20                  25                  30

Cys Val Leu Ala Thr Asn Leu Gln Glu Ile Arg Asn Gly Phe Ser Asp
        35                  40                  45

Ile Arg Gly Ser Val Gln Ala Lys Asp Gly Asn Ile Asp Ile Arg Ile
```

```
            50                  55                  60
Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys His Ala
                115                 120                 125

His Met Thr Cys His Gly Glu Glu Ala Met Lys Lys Tyr Ser Gln Ile
130                 135                 140

Leu Ser His Phe Glu Lys Leu Glu Pro Gln Ala Ala Val Val Lys Ala
145                 150                 155                 160

Leu Gly Glu Leu Asp Ile Leu Leu Gln Trp Met Glu Glu Thr Glu
                165                 170                 175

<210> SEQ ID NO 2
<211> LENGTH: 151
<212> TYPE: PRT
<213> ORGANISM: Homo sapiens

<400> SEQUENCE: 2

Met Lys Ala Ser Ser Leu Ala Phe Ser Leu Leu Ser Ala Ala Phe Tyr
  1                   5                  10                  15

Leu Leu Trp Thr Pro Ser Thr Gly Leu Lys Thr Leu Asn Leu Gly Ser
                 20                  25                  30

Cys Val Leu Ala Thr Asn Leu Gln Glu Ile Arg Asn Gly Phe Ser Asp
                 35                  40                  45

Ile Arg Gly Ser Val Gln Ala Lys Asp Gly Asn Ile Asp Ile Arg Ile
 50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys Leu Glu
                115                 120                 125

Pro Gln Ala Ala Val Val Lys Ala Leu Gly Glu Leu Asp Ile Leu Leu
130                 135                 140

Gln Trp Met Glu Glu Thr Glu
145                 150

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctccagattt caggcctaag atg                                           23

<210> SEQ ID NO 4
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
attgaagact ggagctcttg acc                                             23

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcgaattcg ttccctgtgt ctctggt                                         27

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (8)
<223> OTHER INFORMATION: inosine

<400> SEQUENCE: 6
ttnagccntg aactctgatg                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggctgagat ggacagaatg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccttccgcaa acctatgaga                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
```

-continued

```
gagatgtgat gaaggagatg g                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagcaagctc gcaaccttga                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acttcaagga ccccaagcgg                                                20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctttctgcc caggtcctg                                                 19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtggtgaagt tcatggatgt c                                              21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacgtctgcg gatcttgtac                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagcagcacg tggagctgta                                                20
```

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggcccacgt agtacacgat                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caagggtaca gcctgttcct                                               20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttccctgcaa agaacacagc c                                             21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acatcttcga cgccatcgcg                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aactcacgcg ccagtagaag                                               20
```